United States Patent [19]

Lauffer et al.

[11] Patent Number: 5,250,285
[45] Date of Patent: Oct. 5, 1993

[54] HYDROXY-ARYL METAL CHELATES FOR DIAGNOSTIC NMR IMAGING

[75] Inventors: Randall B. Lauffer; Scott K. Larsen, both of Boston, Mass.

[73] Assignee: The General Hospital Corporation, Boston, Mass.

[21] Appl. No.: 840,652

[22] Filed: Feb. 20, 1992

Related U.S. Application Data

[63] Continuation of Ser. No. 399,737, Aug. 28, 1989, abandoned, which is a continuation-in-part of Ser. No. 860,540, May 7, 1986, abandoned, which is a continuation-in-part of Ser. No. 731,841, May 8, 1985, Pat. No. 4,899,755.

[51] Int. Cl.$^5$ .......................... A61K 49/00; A61B 6/00
[52] U.S. Cl. ........................................ 424/9; 128/654; 128/653.4; 436/173; 514/502; 556/45; 556/50; 556/138
[58] Field of Search ....................... 424/9, 2; 436/173; 552/45, 50, 138

[56] References Cited

U.S. PATENT DOCUMENTS

| | | | |
|---|---|---|---|
| 3,632,637 | 1/1972 | Martell | 260/519 |
| 4,472,509 | 9/1984 | Gansow et al. | 436/548 |
| 4,687,658 | 8/1987 | Quay | 424/9 |
| 4,714,607 | 12/1987 | Klaveness | 424/9 |
| 4,746,507 | 5/1988 | Quay | 424/9 |
| 4,834,964 | 5/1989 | Rosen | 424/9 |
| 4,859,451 | 8/1989 | Quay et al. | 424/9 |
| 4,880,008 | 11/1989 | Lauffer | 128/654 |
| 4,885,363 | 12/1989 | Tweedle et al. | 548/468 |
| 4,899,755 | 2/1990 | Lauffer et al. | 128/654 |
| 4,963,344 | 10/1990 | Gries et al. | 424/9 |

FOREIGN PATENT DOCUMENTS

| | | |
|---|---|---|
| 0258616 | 6/1987 | European Pat. Off. . |
| 0230893 | 7/1987 | European Pat. Off. . |
| 0232751 | 8/1987 | European Pat. Off. . |
| 0292761 | 3/1988 | European Pat. Off. . |
| 0290047 | 4/1988 | European Pat. Off. . |
| 0290041 | 8/1988 | European Pat. Off. . |
| 0292689 | 9/1988 | European Pat. Off. . |
| WO-A-8901476 | 2/1989 | European Pat. Off. . |
| WO-A-8912631 | 12/1989 | European Pat. Off. . |
| 90914613 | 5/1992 | European Pat. Off. . |
| WO-A-8602352 | 4/1986 | PCT Int'l Appl. . |
| WO-A-8901475 | 2/1989 | PCT Int'l Appl. . |

OTHER PUBLICATIONS

Lauffer, Chem. Rev. 87: 901, 1987.
Brittain et al., Inorg. Chem. 23: 4459, 1984.

(List continued on next page.)

*Primary Examiner*—Frederick E. Waddell
*Assistant Examiner*—T. J. Criares
*Attorney, Agent, or Firm*—Fish & Richardson

[57] ABSTRACT

An NMR contrast agent composition contains a complex of a selected metal ion and a selected ligand. The ion is selected from the group consisting of gadolinium (III), iron (III), manganese (II), manganese (III), chromium (III), copper (II), dysprosium (III), terbium (III), holmium (III), erbium (III), europium (II), and europium (III); and the ligand is a linear two-nitrogen compound having one 2 hydroxy-aryl group at one of the nitrogens; or the ligand is a linear two-nitrogen compound having one or two 2-hydroxy aryl groups at each of the nitrogens; or the ligand is a linear three-, four-, or five nitrogen compound having one or two 2-hydroxy-aryl substituents at each of one or more of the nitrogens, or the ligand is a heterocyclic compound having a ring containing three or four nitrogens, and having a 2 hydroxy aryl substituents at one or more of the nitrogens; or the ligand is a heterocyclic compound having a ring containing 4 nitrogens, and having a carboxyl group at two of the nitrogens and an aromatic substituent at the other two of the nitrogens. Also, a method for enhancing the contrast in NMR imaging in a patient includes steps of preparing an NMR contrast enhancing agent by mixing an NMR contrast compound of the invention with a pharmaceutically acceptable carrier, introducing the NMR contrast enhancing agent into the patient, and subjecting the patient to NMR imaging.

9 Claims, 1 Drawing Sheet

OTHER PUBLICATIONS

Martell, "The Design and Synthesis of Chelating Agents", p. 67 in Martell et al., eds., Development of Iron Chelators for Clinical Use, Elsevier North Holland, Inc., 1981.
Davison, "Protein Binding" in La Du et al., eds., Fundamentals of Drug Metabolism and Drug Disposition, R. E. Krieger Pub. Co., Malabar, Fla. 1971 Rocklage et al., Inorg. Chem. 28: 477, 1989.
Taliaferro et al., Inorganica Chimica Acta, 85: 9, 1984.
Taliaferro et al., Inorg. Chem 23: 1188, 1984.
Rocklage et al., Inorg. Chem 27: 3530, 1988.
Lauffer et al., J.A.C.S. 109: 2216, 1987.
Moore et al., Inorg. Chem. 28: 1504, 1989.
Konishiroku Photo Industry Co., Ltd., 74-Radiation Chem; Photochem, vol. 101, p. 537, abstract 219677p, 1984.
Taliaferro et al., New Multidentate Ligands. XXIV. Disodium-N,N'bis(2-hydroxy-5-sulfobenzyl)ethylenediamine diacetic acid, . . . trivalent metal ions, Chemical Abstracts 101:369 No. 44224j, 1984.
Phenolic derivatices of (hydroxyalkyl)alky=-lenediamineacetic acids and their salts, Chemical Abstracts 89:561, 1978.
Martell et al., Inorganica Chimica Acta, vol. 138, 1987, pp. 215-230.

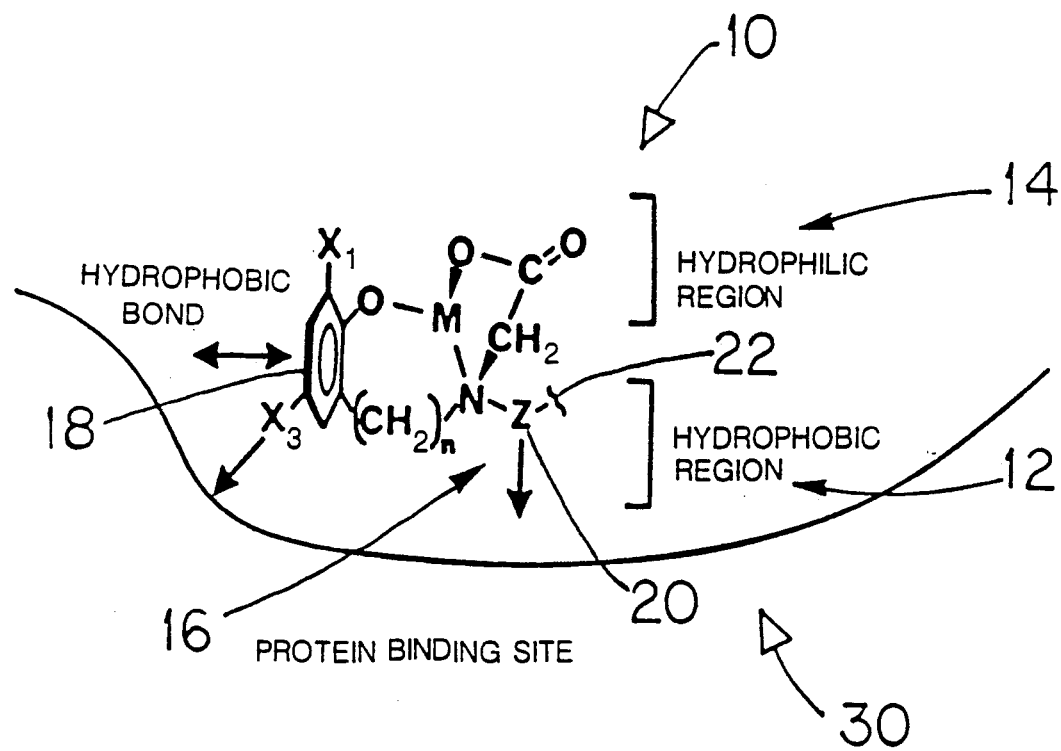
FIGURE

HYDROXY-ARYL METAL CHELATES FOR DIAGNOSTIC NMR IMAGING

BACKGROUND OF THE INVENTION

This is a continuation of application Ser. No. 07/399,737, filed Aug. 28, 1989, now abandoned, which is a continuation-in-part of co-pending U.S. patent application Ser. No. 860,540, filed May 7, 1986 now abandoned, which is a continuation-in-part of co-pending U.S. patent application Ser. No. 731,841, filed May 8, 1985.

This invention relates to diagnostic NMR imaging.

The utility of nuclear magnetic resonance ("NMR") imaging in diagnostic medicine has recently been improved by the development of pharmaceutical NMR contrast agents which change the relaxation times of water protons in the vicinity of the agent. A pharmaceutical NMR contrast agent is selected to bind to a component of a body tissue under study, thereby increasing the relaxivity of water protons in the vicinity of the tissue to which the agent is bound. In this way the NMR signal from the tissues of interest is enhanced relative to the surrounding tissues.

SUMMARY OF THE INVENTION

The present invention provides tissue specific NMR contrast enhancing agents which are capable of increasing the relaxivity (that is, decreasing NMR relaxation times $T_1$ or $T_2$) of water protons in contact with the biological tissue. The NMR contrast agents of the invention incorporate 2 hydroxy aryl groups into metal chelating ligands to produce metal ion chelate NMR contrast agents which preferentially bind to specific proteins in a non-covalent and non-immunologic manner. As a result of this binding the protons of the water molecules in the vicinity of the metal ion chelates have a relaxivity that is enhanced by at least a factor of two relative to the relaxivity induced by the paramagnetic complex free in solution.

The tissue specificity of the NMR contrast agents of the invention is due in part to the structure of the metal ion chelate and its ability to mimic the structure of naturally occurring molecules which have an affinity for the tissue of interest. Further, the binding of the metal ion chelates to such tissues is enhanced by the incorporation of substituents which increase the lipophilicity and hydrophobicity of specific portions of the molecule.

Some of the metal ion chelates of the invention mimic the structure of bilirubin and thereby exhibit preferential binding to albumin, to the hepatocellular uptake protein, to ligandin, and to the fatty acid binding proteins. The ability of the chelates of the invention to bind to these proteins renders them useful in enhancing the image of normal liver tissue in the presence of tumors, for monitoring liver function, and for enhancing the image of the bile ducts and gallbladder. In addition, binding to albumin in the blood creates a high relaxivity blood pool contrast agent that is useful in detecting disruption of the blood-brain barrier, in NMR angiography, in perfusion imaging, and in distinguishing between tumors and blood filled lesions such as hemangiomas and hemorrhage.

The invention features, in one aspect, an NMR contrast agent composition containing a complex of a selected metal ion and a selected ligand. In each complex the ion is selected from the group consisting of gadolinium (III), iron (III), manganese (II), manganese (III), chromium (III), copper (II), dysprosium (III), terbium (III), holmium (III), erbium (III), europium (II), and europium (III); and the ligand is a linear two nitrogen compound having one 2 hydroxy-aryl group at one of the nitrogens; or the ligands is a linear two-nitrogen compound having one or two 2-hydroxy-aryl groups at each of the nitrogens; or the ligand is a linear three-, four-, or five-nitrogen compound having one or two 2-hydroxy-aryl substituents at each of one or more of the nitrogens, or the ligand is a heterocyclic compound having a ring containing three or four nitrogens, and having a 2-hydroxy-aryl substituent at one or more of the nitrogens; or the ligands is a heterocyclic compound having a ring containing 4 nitrogens, and having a carboxyl group at two of the nitrogens and an aromatic substituent at the other two of the nitrogens.

Linear two-nitrogen ligands of the invention which include a single aryl group have the general structure:

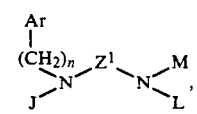

where n is 0 or 1;
each J, L, M, independently, is

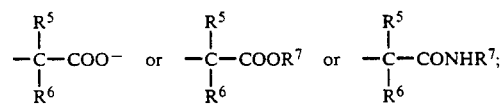

the aryl group (Ar) is one of

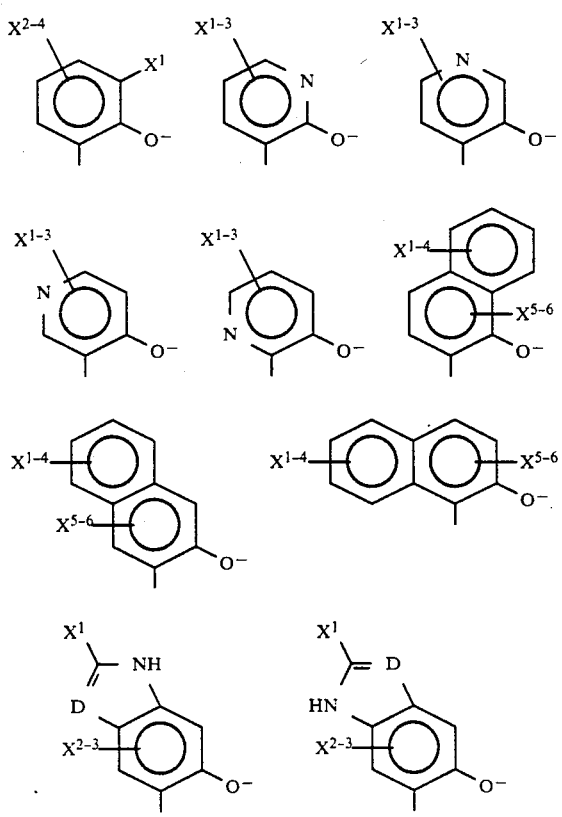

-continued

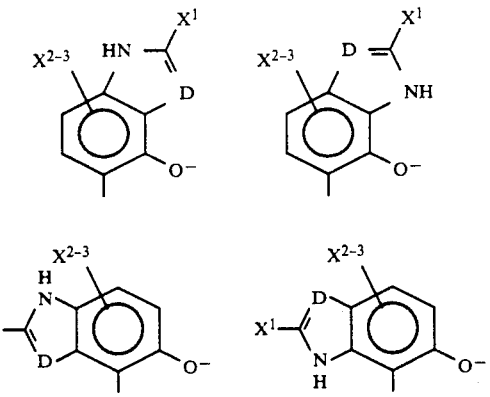

$Z^1$ is one of

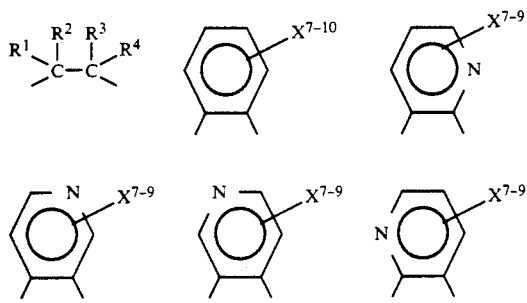

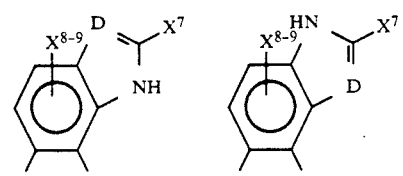

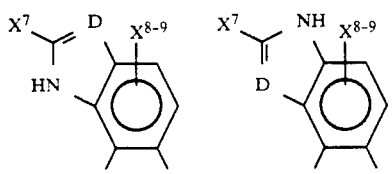

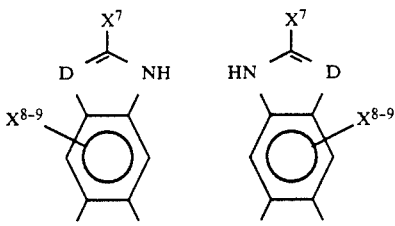

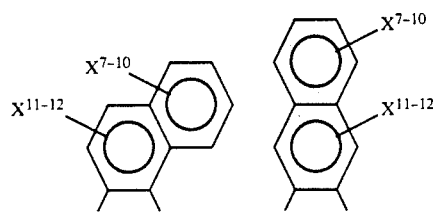

-continued

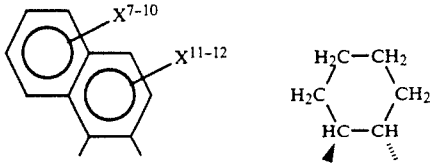

in which D is one of —CH= or —N=,
each $X^{1-12}$, independently, is one of H, or $C_{1-10}$ alkyl, or $C_{1-15}$ arylalkyl, or halogen, or —(CH$_2$)$_m$COO$^-$, or —(CH$_2$)$_m$CONHR$^8$, or —(CH$_2$)$_m$COOR$^8$, or —(CH$_2$)$_m$COH, or —SO$^-_3$,
where m is an integer from 0–5;
and each $R^{1-8}$, independently, is one of H, or $C_{1-10}$ alkyl, or $C_{1-15}$ arylalkyl.

Because of their molecular orientation and crystal packing forces, linear two-nitrogen, two 2-hydroxy-aryl chelates present particular solubility problems For example, iron bis(5-bromo-2-hydroxybenzyl)-ethylenediaminediacetate ("Fe-5-BrHBED") has proven to be inadequate as: an NMR contrast agent because it precipitates out of aqueous solution with time. This may stem from pi-pi intermolecular interactions between the two benzene rings of one molecule and those of another; since the two rings on each molecule are relatively planar to one another, the stacking events are cooperative and highly efficient. Molecular models of those other chelates of this invention that have two benzene rings (linear three- to five-nitrogen compounds, cyclic three- to four-nitrogen compounds) do not show the same planar orientation of the rings as is present in HBED chelates.

For these reasons, the linear two-nitrogen, two 2-hydroxy-aryl chelates of the invention must have hydrophilic substituents placed ortho to the aryl hydroxy ($X_1$ substituents in the structural diagram above).

Linear two-nitrogen ligands of the invention which include two aryl groups have the general form

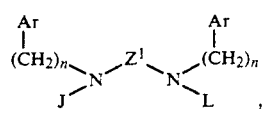

where n is 0 or 1;
each J, L, independently, is

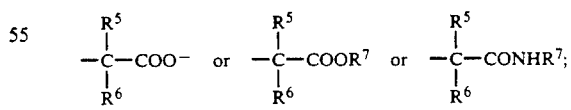

the aryl groups (Ar) are each one of

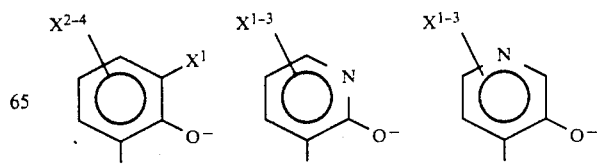

-continued

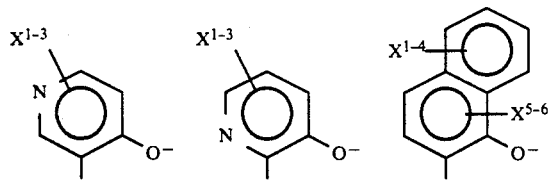

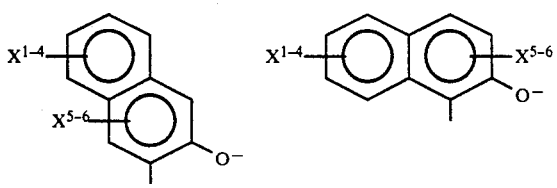

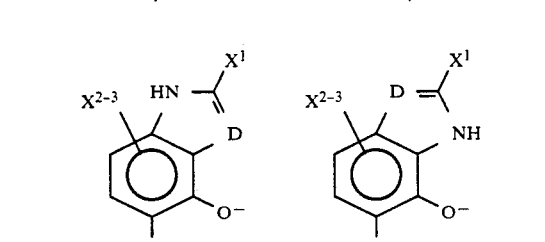

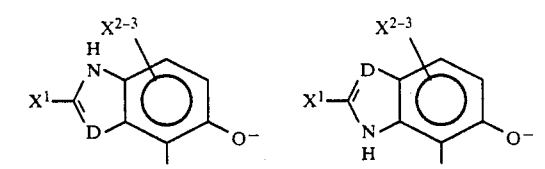

Z' is one of

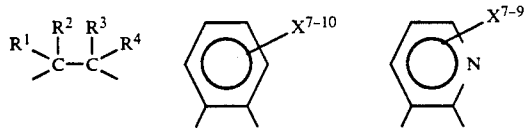

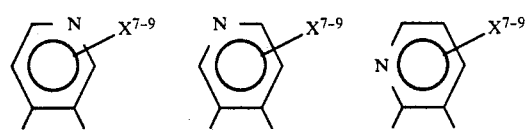

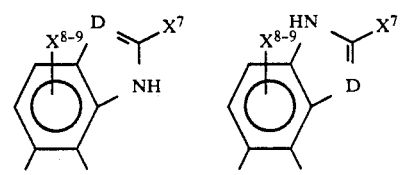

-continued

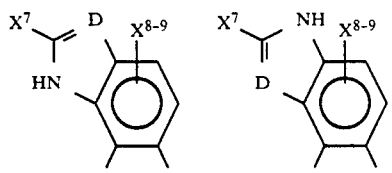

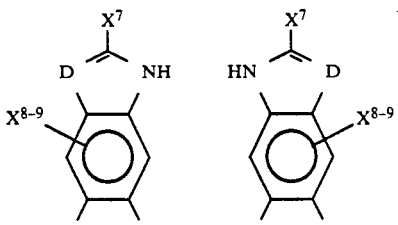

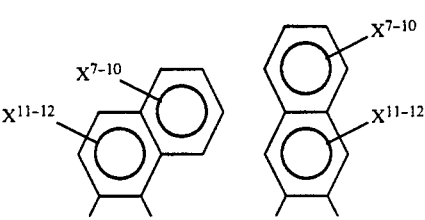

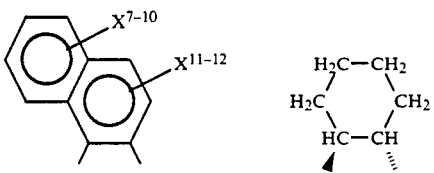

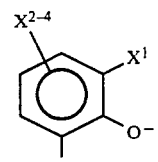

in which D is one of —CH= or —N=,
each $X^{1-12}$, independently, is one of H, or $C_{1-10}$ alkyl, or $C_{1-15}$ arylalkyl, or halogen, or —$(CH_2)_m COO^-$, or —$(CH_2)_m CONHR^8$, or —$(CH_2)_m COOR^8$, or —$(CH_2)_m COH$, or —$SO^-_3$, where m is an integer from 0-5,
provided that, where the aryl groups (Ar) have the form $X^1$ is one of
—$(CH_2)_m COO^-$, or
—$(CH_2)_m CONHR^3$, or
—$(CH_2)_m COOR^9$, or
—$(CH_2)_m COH$, or
—$SO^-_3$,
and each $X^{2-4}$, independently, is one of
H, or $C_{1-10}$ alkyl, or
$C_{1-10}$ arylalkyl, or halogen;
and each $R^{1-9}$, independently, is one of H, or $C_{1-10}$ alkyl, or $C_{1-15}$ arylalkyl.

Linear three- to five-nitrogen ligands of the invention have the general structure

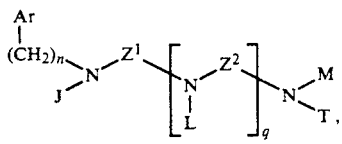

where q is an integer from 1-3;
each J, L, M, T, independently, is

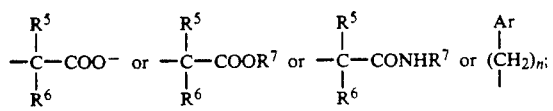

n is 0 or 1;
the aryl group (Ar) is one of

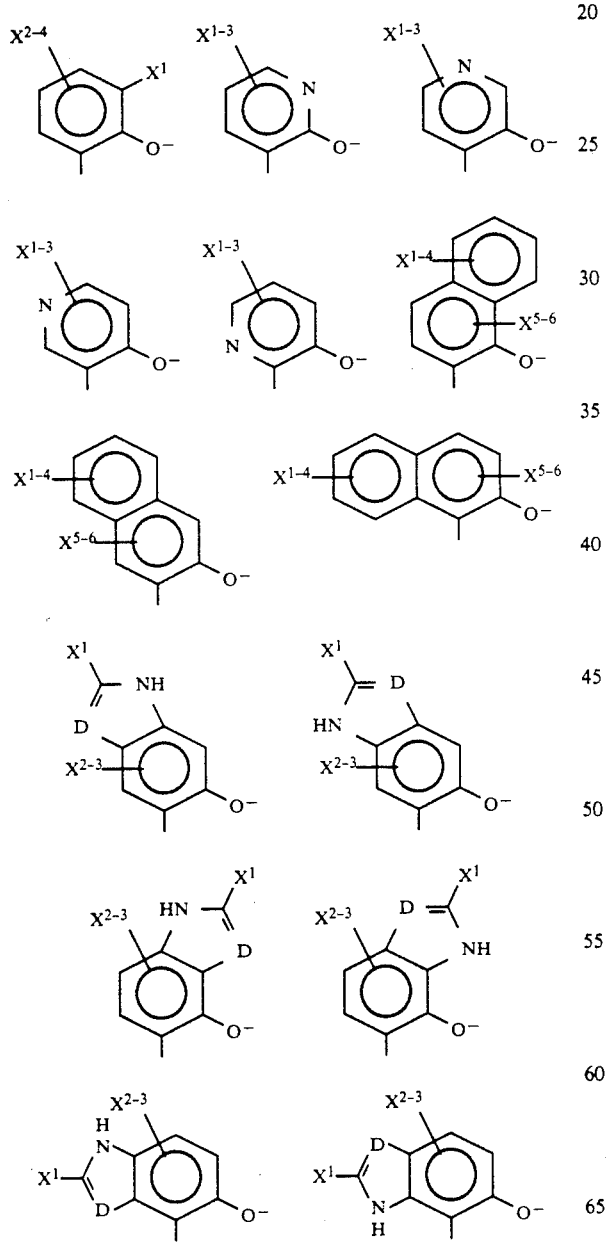

each $Z^{1,2}$, independently, is one of

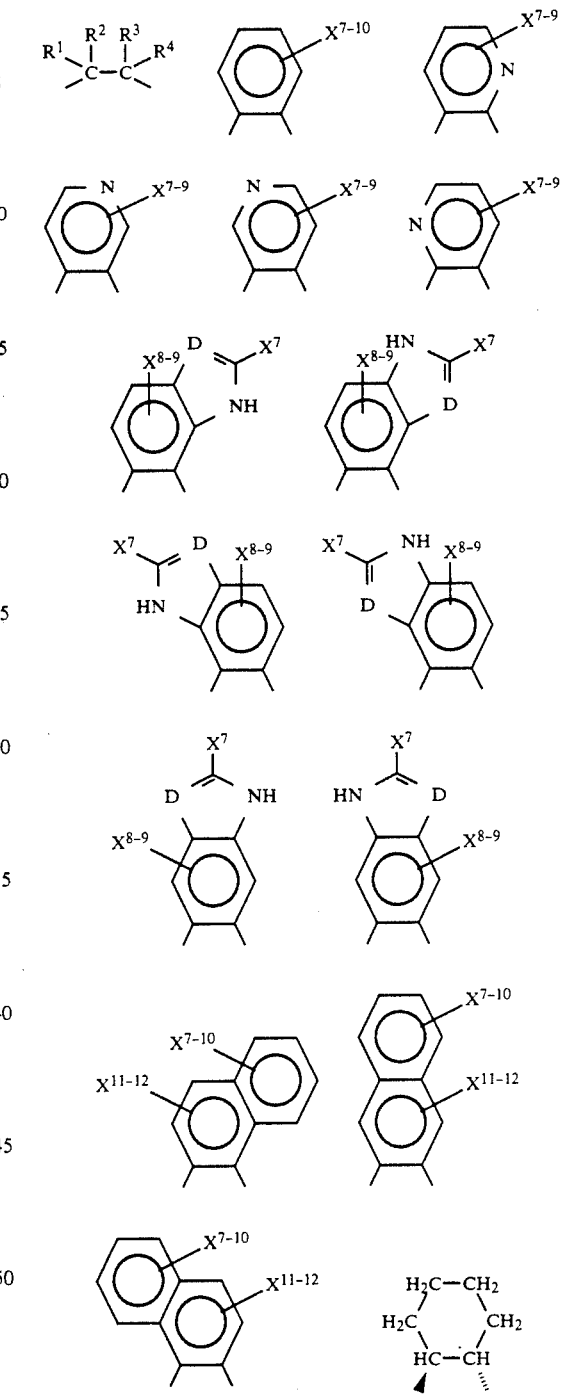

in which D is one of —CH= or —N=,
each $X^{1-12}$ independently, is one of H, or $C_{1-10}$ alkyl, or $C_{1-15}$ arylalkyl, or halogen, or —$(CH_2)_m COO^-$, or —$(CH_2)_m CONHR^8$, or —$(CH_2)_m COOR^8$, or —$(CH_2)_m COH$, or —$SO^-_3$, where m is an integer from 0-5;
and each $R^{1-8}$, independently, is one of H, or $C_{1-10}$ alkyl, or $C_{1-15}$ arylalkyl.

Cyclic three-nitrogen ligands of the invention, which are large enough to constrain the selected paramagnetic metal ion, have the general structure

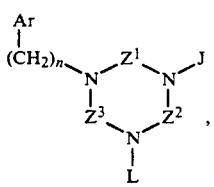

where each J, L, independently, is

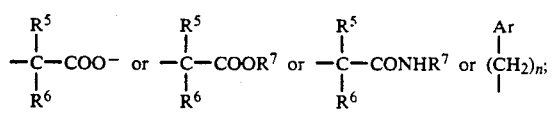

n is 0 or 1;
the aryl group (Ar) is one of

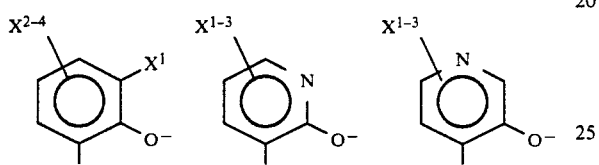

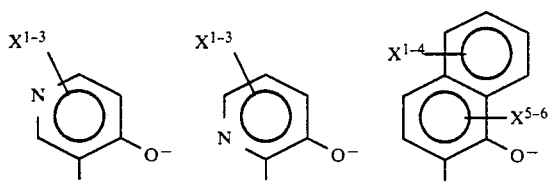

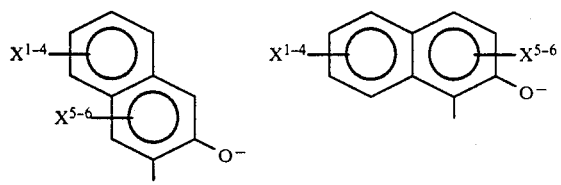

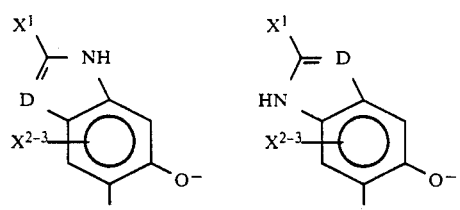

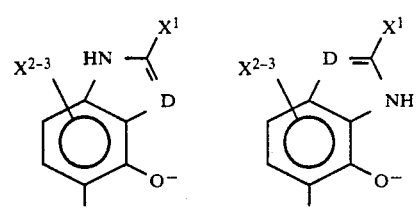

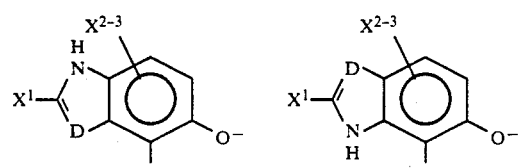

each $Z^{1-3}$, independently, is one of

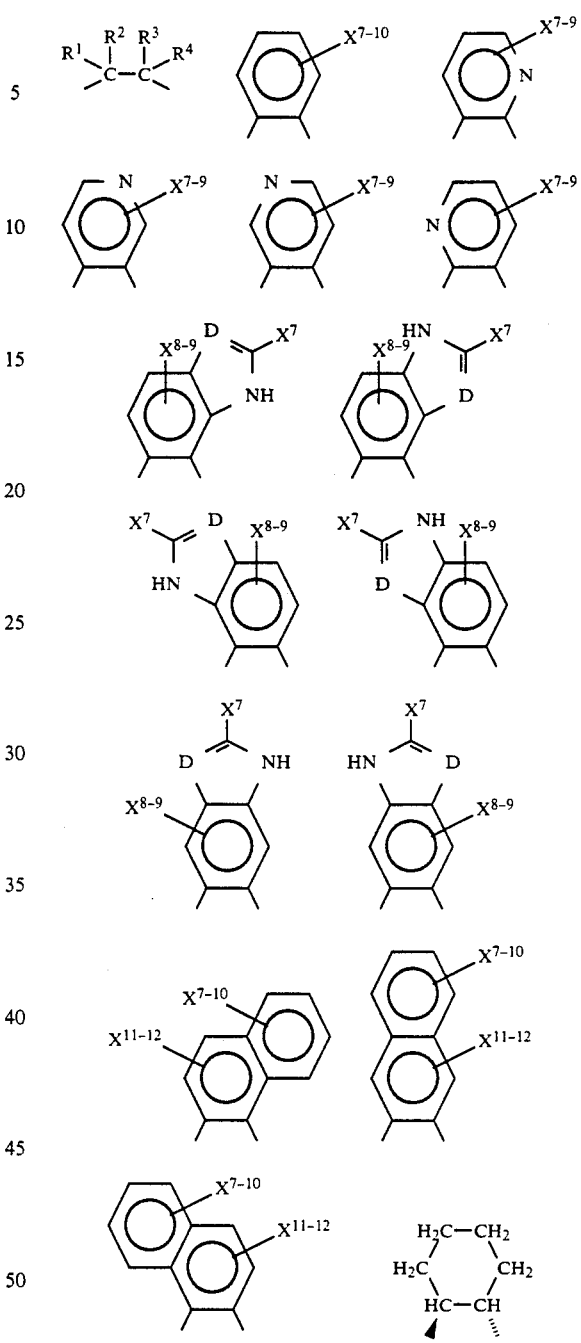

in which D is one of —CH= or —N=,
each $X^{1-12}$, independently, is one of H, or $C_{1-10}$ alkyl, or $C_{1-15}$ arylalkyl, or halogen, or —$(CH_2)_m COO^-$, or —$(CH_2)_m CONHR^8$, or —$(CH_2)_m COOR^8$, or —$(CH_2)_m COH$, or —$SO^-_3$,
where m is an integer from 0-5;
each $R^{5,6}$, independently, is one of H, or $C_{1-5}$ alkyl;
and each $R^{1-4, 7, 8}$, independently, is one of H, or $C_{1-10}$ alkyl, or $C_{1-15}$ arylalkyl
provided that, when both J and L are 2-hydroxyl-aryl substituents, at least one Ar must be substituted at the position ortho to the aryl hydroxy group with a hydrophilic $X^1$, one of
—$(CH_2)_m COO^-$, or
—$(CH_2)_m CONHR^9$, or —$(CH_2)_mCOOR^9$, or
—$(CH_2)_mCOH$, or
—$SO_3^-$.

Tri aryl ligands having three nitrogens in the backbone, absent a hydrophilic $X^1$ substituent, as described further below, are unsuitable for use in complexes with trivalent metal ions (the most important of which are Fe(III) and Cr(III)) as NMR contrast agents, as such complexes would be electrically neutral and therefore not sufficiently soluble for administration.

On the other hand, the hexadentate ligand NOTA, known to be an excellent chelating agent for transition metal ions, with association constants on the order of log K>17, would not be suitable in metal complexes for liver or blood-pool imaging as they lack the hydrophobic substituents required for protein binding.

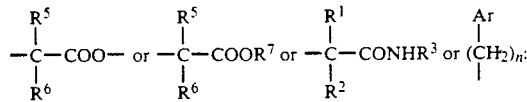

For these reasons, the cyclic three-nitrogen chelates of the invention must have an aryl substituent on at least one of the backbone nitrogens.

Cyclic four-nitrogen ligands of the invention, which are large enough to constrain the selected paramagnetic metal ion, have the general structure

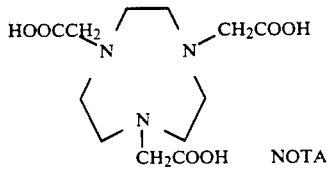

each J, L, M, independently, is

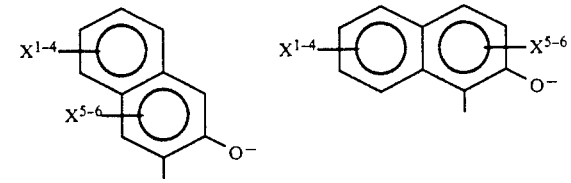

n is an 0 or 1;
the aryl group (Ar) is one of

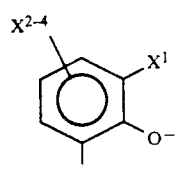 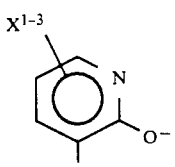 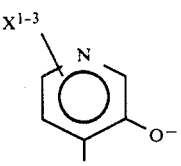

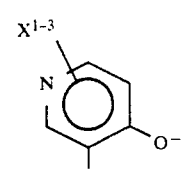 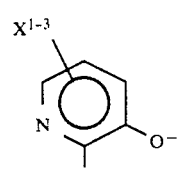 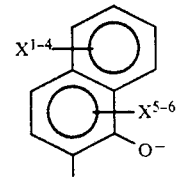

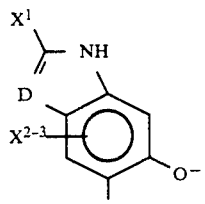 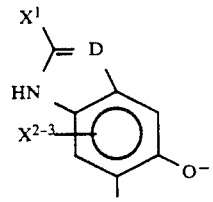

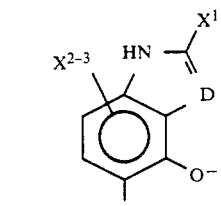 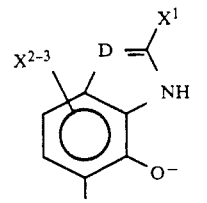

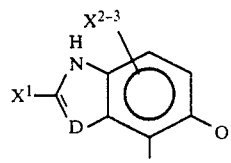 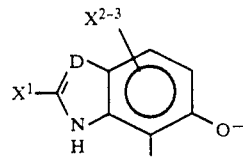

each $Z^{1-4}$, independently, is one of

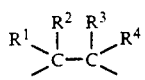 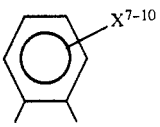 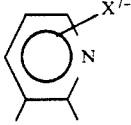

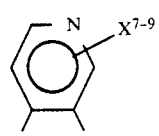 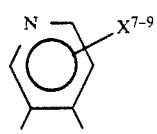 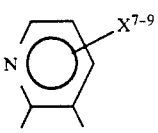

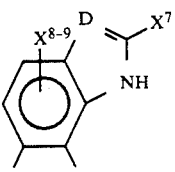 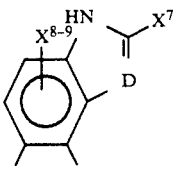

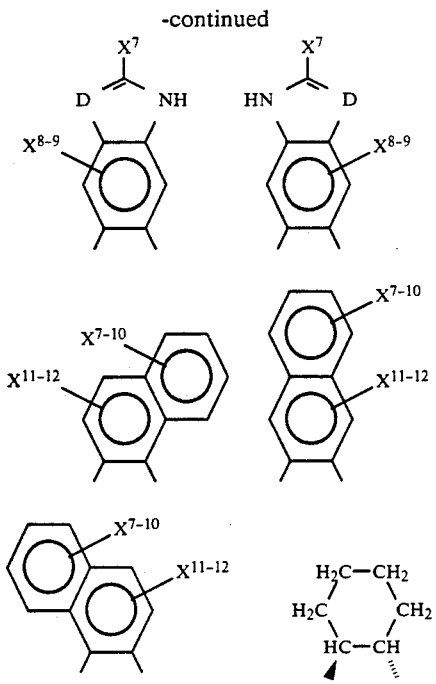

in which D is one of —CH= or —N=,
each $X^{1\text{-}12}$, independently, is one of H, or $C_{1\text{-}10}$ alkyl, or $C_{1\text{-}15}$ arylalkyl, or halogen, or —$(CH_2)_m COO^-$, or —$(CH_2)_m CONHR^{89}$, or —$(CH_2)_m COOR^8$, or —$(CH_2)_m COH$, or —$SO^-_3$, where m is an integer from 0–5;
each $R^{5, 6}$, independently, is one of H, or $C_{1\text{-}5}$ alkyl; and each $R^{1\text{-}4, 7, 8}$, independently, is one of H, or $C_{1\text{-}10}$ alkyl, or $C_{1\text{-}15}$ arylalkyl.

The cyclic four-nitrogen chelates of the invention are suitable, for example, for blood-pool imaging, as they contain hydrophobic regions which provide for good solubility, they are excellent chelators for metal ions, and they contain hydrophobic substituents required for binding to blood proteins such as albumin. In contrast, the octadentate ligand DOTA, which is a known chelating agent for lanthanide ions, having association constants in the order of log K>20, lacks hydrophobic substituents and as such is unsuitable for NMR image enhancement of the liver and blood pool.

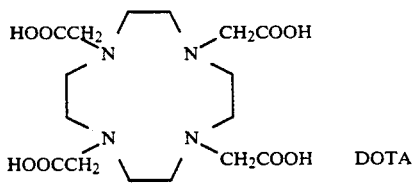

For these reasons, the cyclic four-nitrogen chelates of the invention have an aryl group on at least one of the nitrogens.

The invention features, in another aspect, a method for enhancing the contrast in NMR imaging in a patient, including steps of preparing an NMR contrast enhancing agent by mixing an NMR contrast compound of the invention with a pharmaceutically acceptable carrier; orally, intravascularly or intraperitoneally introducing the NMR contrast enhancing agent into the patient subjecting the patient to NMR imaging.

DESCRIPTION OF THE PREFERRED EMBODIMENTS

Drawing

The Figure is a schematic diagram showing general features of a metal ion chelate of the invention in relation to a protein to which the chelate is bound non-covalently.

STRUCTURE

Some NMR contrast agents of the invention remain in the blood stream and thereby act as contrast agents for the vascular system. Others are taken up by the liver and act as contrast agents for the liver and the ducts of the hepatobiliary system. To be effective, chelates for use as vascular imaging agents must not be quickly excreted by the kidneys, nor diffuse from the capillaries into the interstitial space. Those for use as hepatic imaging agents must be actively taken up by the liver and excreted in the bile. One property which confers these capabilities on an NMR contrast agent is an ability of the agent to bind to proteins. By binding to circulating proteins, such as human serum albumin (HSA), the agent can be made to remain in circulation. Similarly, by binding to specific proteins in the hepatocytes, such as the hepatocellular uptake protein, or ligandin (glutathione-s-transferase), or the fatty acid binding protein, the contrast agent can be concentrated in the liver, and can exhibit increased relaxation efficiency near the hepatocytes by virtue of the specific binding.

For the agent to act as a tissue specific NMR contrast agent, the agent must alter the relaxation times ($T_1$, longitudinal and/or $T_2$, transverse) of water protons near the tissue to which the agent is bound. To do this, the agent must contain a paramagnetic ion of the transition metal or lanthanide elements and must have at least one, and preferably five or more, unpaired electrons and a magnetic moment of at least 1.7 Bohr magnetons. Preferred ions are gadolinium (III), iron (III), and manganese (II); other suitable ions include manganese (III), chromium (III), copper (II), dysprosium (III), terbium (III), holmium (III), erbium (III), europium (II), and europium (III).

In the NMR contrast agents of the invention, these paramagnetic ions are associated with ligands which are large enough to incorporate the paramagnetic ion, and which also confer other important characteristics, such as protein binding specificity, on the agent. The structure of the ligand confers on the metal chelate not only its protein binding capability but also the strength of the metal-ligand bonding. A number of considerations enter into the design of the metal ion chelates used in the NMR contrast agents of the invention.

Because the bond between the metal chelate and the protein is non-covalent, binding is promoted by the existence of hydrophobic regions in both the metal chelate and the protein to which it is targeted. 2-hydroxy-aryl groups possess the necessary hydrophobicity and pi ($\pi$) electron character to interact with the hydrophobic sites in the protein. Further, an aryl group which is bound to the protein at multiple contact points aids in preventing free rotation of the complex, thereby adding to the rigidity of the non-covalent bond with a resulting increase in relaxivity.

The presence of a net charge on the metal ion chelate contributes an electrostatic interaction to the binding of the chelate with charged regions on the protein. For example, HSA has positively charged regions to which a negatively charged chelate may bind.

The presence of hydrophilic groups on the chelate contributes to its solubility. To be effective in an NMR contrast agent the chelate must be soluble enough to maintain a concentration of at least 1 mM in normal saline or any other pharmaceutically acceptable solvent or formulation.

The increased proton relaxivity imparted by the chelate is optimal where the paramagnetic complex has one or more open coordination sites available for water exchange. Generally the presence in the complex of more than two open coordination sites is not desired because of increased toxicity, as discussed more fully below. A metal chelate having no open coordination sites can be acceptable, but is not preferred.

To be effective in an NMR contrast agent the combined ion and ligand must additionally exhibit low toxicity at dosages used for NMR contrast enhancement. In constructing these contrast agents, the problem of toxicity can be addressed by using an inherently less toxic paramagnetic ion, or by selecting a chelating agent which has a low degree of dissociation and thereby has a lesser tendency to release the toxic ion, or by selecting a metal ion chelate which has a lower number of open coordination sites and thereby has a lesser tendency to release the ion. Generally a chelating agent with more open sites may be used in combination with either a less toxic ion or with an ion having a higher magnetic moment (resulting in a lower dosage being required for effectively enhancing the image), and a chelating agent having no open coordination sites may be used with a more toxic ion or with one having a higher magnetic moment. For example, the cytotoxic hydroxyl radical forms by the Fenton reaction in the presence of superoxide and iron complexes having open coordination sites, and so iron should be used with a chelating agent having no open coordination sites in order to minimize toxicity. The gadolinium ion, on the other hand, with seven unpaired electrons, can be used with a chelating agent having a number of open sites, and can act as a contrast agent at very low dosages, and be no more toxic than iron used with a chelating agent having no open sites.

One class of metal chelates having these properties mimics the structure of bilirubin, which is known to bind to albumin, to the hepatocellular uptake protein, to ligandin, and to fatty acid binding proteins. By incorporating 2-hydroxy-aryl groups into these metal chelating ligands, which have from two to five nitrogen atoms, the binding affinity of the metal chelate to the protein is affected and hence so is the distribution of the contrast agent.

Specifically, for example, it is known that phenolate type groups are more polarizable and more hydrophobic, and molecules that contain phenolate anions bind well to proteins. Although the non-covalent interaction between proteins and phenolate anion-containing molecules is not well understood, it is suggested that the oxygen acts as an electron donor to the benzene ring and that this contributes to the non-covalent binding properties.

The molecules of the invention include highly stable five and six member 2-hydroxy-aryl groups as part of the chelating arms. This results in a structure that not only has good protein binding properties but also has an ability to bind to the metal ions.

The presence of the hydroxyl substituent on the aryl group is important because, as noted above, the oxygen can act as an electron donor to the ring. Further, an ortho placement of the hydroxyl group on the aryl ring is important in that it can allow the oxygen to be in a position to bind to the metal ion. In addition to stabilizing the metal ion within the chelate, this oxygen metal ion binding neutralizes some of the charge on the oxygen, and can make that portion of the molecule somewhat more hydrophobic and, hence, capable of binding more strongly to the protein.

In addition, other negatively charged substituents, such as acetate or sulfate groups, may be placed on the ring, preferably ortho to the hydroxyl group, to create a negative charge which can aid the binding of the chelate to proteins such as albumin and can also contribute to the solubility of the compound.

The Figure shows, in highly schematic form, the general features of the chelates of the invention that are important in selecting and positioning substituents in the structure. A portion 10 of a chelate of the invention is shown in positional relationship to a site 30 on a protein to which the chelate is configured to bind. In order both to interact with a protein binding site and to be soluble enough for human administration, the metal complex must have both hydrophobic and hydrophilic regions. The chelate portion 10 includes a hydrophobic region generally indicated at 12, which extends into the protein (downward in the Figure) and binds to the protein at the chelate binding site 30; and a hydrophilic region generally indicated at 14, which extends generally away from the chelate binding site 30 (upward in the Figure).

As shown in the Figure, the (downward-facing) hydrophobic region 12 of a chelate of the invention is structured to generally conform to the configuration of the binding site 30, and includes the bottom portion of the chelate, generally indicated at 16, joined at a nitrogen to a 2 hydroxy aryl ring 18. The bottom portion of the chelate includes a variable Z region 20 which, together with the nitrogen, forms the backbone of the molecule, described more fully below. Further portions of the chelate, containing appropriately-positioned hydrophobic and hydrophilic substituents and further backbone nitrogens, as described more fully below, and thereby contributing further to the hydrophobic and hydrophilic regions of the chelate, can be attached to the variable Z region, as indicated at 22. Additional portions of the metal chelate can contribute further 2 hydroxy aryl rings and further carboxylates, as well as further nitrogens in the backbone of the molecule. It can be preferable for some chelates to place additional hydrophobic substituents in appropriate locations on the 2-hydroxy-aryl ring 18 or on the variable Z portion 20 to further extend the hydrophobic region 12 into the protein binding site 30 and thereby increase protein binding affinity. Appropriate locations on the 2-hydroxy aryl ring include positions metal and para with respect to the hydroxy group, preferably the para position, as indicated in the Figure as hydrophobic substituent $X^3$.

The (upward-facing) hydrophilic region 14 of the chelate includes the oxygen of the hydroxy group on the 2-hydroxy-aryl ring, and the oxygen of the acetate group on the nitrogen of the backbone. These heteroatoms possess lone electron pairs which hydrogen bond to water molecules and thereby increase the solubility of the chelate. In certain chelates, particularly those that are electrically neutral, or those that possess several large hydrophobic groups or possess two relatively planar benzene rings, it can be necessary to place additional hydrophilic substituents on the chelate, positioned so as not to inhibit the protein binding affinity. The preferable position is ortho with respect to the hydroxy group on the 2-hydroxyl-aryl ring, shown in the Figure as hydrophilic substituent $X_1$ since this position is within the upwardly-directed hydrophilic region of the chelate.

The metal ion is held particularly by the hydroxy oxygen on the 2-hydroxy-aryl ring and by the nitrogen of the backbone, and also by a carboxy oxygen of the acetate group on the backbone nitrogen. In the backbone substituent —$(CH_2)n$—, n is preferably 0 or 1, as these provide, with the metal ions, highly stable 5-member (—[metal]—O—C—C—N—) or 6-member ([metal]—O—C—C—$CH_2$—N—) ring-shaped chelating constructs.

By proper choice of substituents, as described in this application, the binding affinity of the agent for proteins located in or on the tissue to be examined can be increased, and thus the relaxivity of water proteins in the vicinity of the tissue can be increased, enhancing the NMR signal from the tissue.

The substituents on the aryl group (generally, the "X-substituents") are important for the binding of chelate to the protein. Preferably the X-substituents contain both hydrophobic and negatively charged groups, and, for example, a hydrophobic X-substituent such as, for example, a halogen, contributes to the binding of the agent to the protein, particularly where the hydrophobic substituent is situated para to the oxygen.

Additionally, hydrophobic substituents (halogen or alkyl), particularly when separated from the charged substituent by one or two carbons (positions 5 or 6), can increase the binding affinity to the proteins.

The hydrophobic X-groups (halogen, alkyl, arylalkyl) on the 2-hydroxy-aryl ring, which contribute to the lipophilicity of the aryl ring, are preferably placed closer to the protein binding site (away from the metal binding site), and the negatively charged groups are preferably placed closer to the hydroxyl group. Thus, in a six membered aryl group, for example, position three is the most preferred position for hydrophilic groups. Positions three and six are not equivalent because when the metal ion is bound to the ligand, position six is in the more hydrophobic region of the molecule.

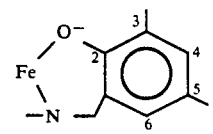

For NMR image enhancement in the liver, for example, hydrophilic and/or anionic substituents are preferably located in the 3 position of the 2 hydroxy aryl ring (ortho to the 2-hydroxy oxygen) rather than in any of positions 4-6, for two reasons. First, with positions 4-6 hydrophobic, they, along with the remainder of the "bottom" or "backbone" portion of the molecule, containing the hydrophobic methylene and ethylene groups, can interact with hydrophobic portions of the chelate binding site on the protein to improve the binding affinity of the agent for the protein; and second, the resulting molecule can be expected to have a conformational similarity to bilirubin, providing for binding specificity of the agent to tissues bound by bilirubin.

An example of such a substituted ligand is bis(5-bromo 3-acetate 2-hydroxybenzyl)ethylenediamine diacetic acid ("BAHBED"). Chelates having the general size and shape of BAHBED are known to bind to the bilirubin site on HSA, and the configuration of chelates having additional or different substituents can be predicted, as described more fully below. For example, the chelate Fe(BAHBED)$^{3-}$, which has two nitrogens in the backbone and two 2 hydroxy-aryl substituents, can mimic the binding characteristics of bilirubin.

The structure of the parent compound of BAHBED, Fe-HBED$^-$, was determined by X-ray crystallography, allowing an accurate prediction of the conformation of Fe(BAHBED)$^{3-}$:

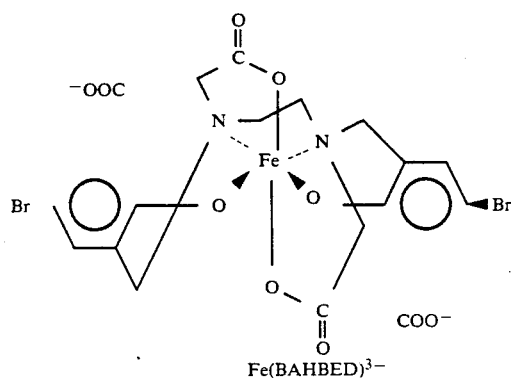

Fe(BAHBED)$^{3-}$

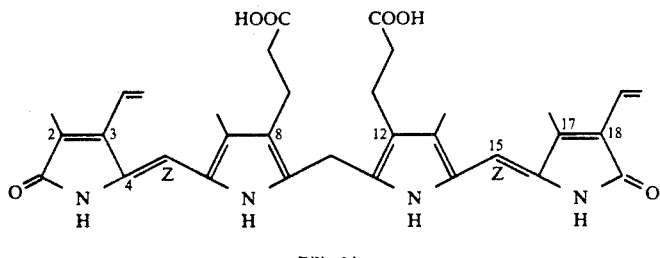

Bilirubin

Analysis of the structure of Fe(BAHBED)$^{3-}$ illustrates the importance of properly positioning the hydrophilic and hydrophobic substituents. The orientations of the two free carboxylates relative to the hydrophobic moieties in Fe(BAHBED)$^{3-}$ provide for a chelate that mimics the conformation of bilirubin.

It is also preferable to have groups which extend the hydrophobic region of the chelate deeper into the protein binding site, and the configuration and size of the backbone portion of the molecule can be adapted for this purpose, particularly by choice of Z constituents. It can be desirable for example, to position NH groups, such as in indole and benzimidazole substituents, into the hydrophobic region in order to increase solubility. NH groups on the hydrophobic substituents may additionally provide hydrogen bonding between the hydrophobic region of the chelate and the binding site on the protein. For example, as bilirubin has hydrogen bonding NH groups, the use of NH groups can increase the binding of a chelate to the bilirubin binding sites on the protein. The use of fused rings, such as indole, as the aryl group of the chelate accomplishes both a deeper penetration of the protein and the placement of the nitrogen into the hydrophobic region.

Larger groups are also important in the R$^3$ position, (off the nitrogen in the chelate ring) and even more important in the R$^8$ position of the negatively charged aryl ring substituents, for example as in a pro-drug form of the carboxylate, which must be metabolized to the active free carboxylate form. Conversely, the larger groups should be avoided in the R$^2$ and R$^1$ positions. Substituents in these positions preferably are limited to 1-5 alkyl or hydrogen, as larger groups may interfere with chelation of the acetate.

Synthesis

All the compounds whose structures are described in this application can be synthesized using standard chemical techniques. Following are examples of reaction sequences that can be used in the construction of chelates of the invention having various numbers and arrangements of nitrogen atoms in the backbone.

Two-Nitrogen Chelates having Two Aryl Groups

To synthesize two-aryl two-nitrogen chelates one combines 2-Y, 4-X substituents of phenol, with formaldehyde and ethylene diamine diacetic acid ("EDDA") in an aqueous solution of methanol and sodium hydroxide to yield a substituted hydroxybenzyl aryl group attached to an ethylene diamine backbone (i.e., N,N' bis(2 hydroxy 3Y-5X-benzyl) ethylene diamine N,N' diacetic acid ("X,Y-HBED")). The reaction is as follows.

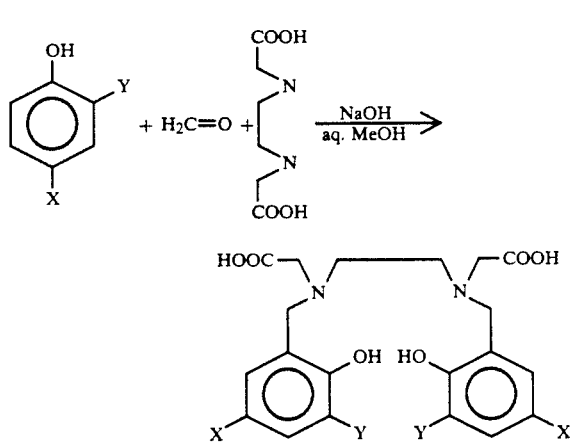

If the 3Y, 5X substituents of the aryl group are carboxylate and bromine, another path is available using the Zaug synthesis to add a methylchloride to 3-bromo salicylic acid. This is then combined with EDDA to yield 5-bromo-3-carboxy HBED. The reaction is as follows.

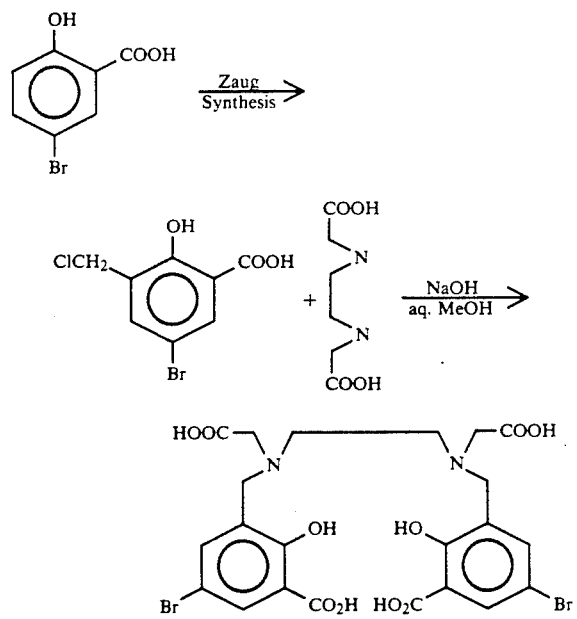

Iron(5 bromo 3 acetate-HBED) ("Fe-BAHBED") is synthesized by the following protocol. 5.23 g (34.37 mmol) of 2-hydroxyphenylacetic acid are dissolved into 150 ml of CCl$_4$ with mild warming. 1.77 ml (34.37 mmol) of Br$_2$ dissolved into 50 ml of CCl$_4$ are added slowly so the color of bromine in the reaction flask never builds up appreciably. The reaction is stirred 20 hrs. The resulting salmon ppt of 5-bromo-2-hydroxy phenylacetic acid ("BHPA") is filtered and recrystallized from water. (The BHPA product has the following characteristics. mp 146°, 68% yield; NMR (DMSO): 3.63 (singlet), 7.54–6.93 ppm (three multiplets); Mass spec.: m/z 230, 232 (1:1) molecular ion.)

5.123 g (22.16 mmol) of BHPA, made as described above, is suspended into 50 ml of 50% aqueous methanol and-.purged with $N_2$. The BHPA is neutralized with 44 mmol of 1M NaOH. 1.963 g (11.14 mmol) EDDA is neutralized with 22 ml of 1M NaOH and upon dissolving, 1.63 ml (22.16 mmol) of 37.9% formaldehyde solution is added. The solution is stirred for 30 min with gentle heating and then diluted with 25 ml methanol. The resulting solution is purged with $N_2$ and added to the BHPA. The final reaction mixture is refluxed under $N_2$ for 48 hrs. After cooling, the solution is neutralized with approximately 22 ml of 1M NaOH and extracted three times with ether. To the aqueous layer 1.81 g (11.14 mmol) $FeCl_3$ dissolved in a few ml of water is added. The resulting red-purple mixture is digested over low heat for 30 min, filtered, adjusted to pH 7 and evaporated. The red solid is chromatographed over neutral silica gel with 70%:5%:25% MeOH:acetic acid:$CHCl_3$ to yield a red-violet solid which is re-chromatographed over a second silica gel column using a solvent gradient of MeOH:acetic acid:$CHCl_3$ of 30:5:65 to 80:0:20. The red-violet band is collected and evaporated. (The Fe(BAHBED) product has the following characteristics. mp>180° decomp., yield 12% $Na_3Fe(BAHBED)$. Paramagnetic $^1H$ NMR (water): 66 ppm (4-H), 39 ppm (6-H) downfield from DSS. Mass spec: FAB(−), 16ug/ul solution in MeOH and TEA, m/z 778:780:782 (1:2:1) molecular ion. UV/VIS: 504 nm (phenol-to-iron charge transfer), 287 nm (phenol pi-pi). Solubility in water: 18 mM.)

Additionally, if the chelate is not simply an aryl addition to ethylene diamine diacetic acid, but instead is to include an aryl within the backbone, the following synthesis is possible. Combining 4,5-Y, diaminobenzene with 2-hydroxy, 5-X, benzaldehyde in the presence of sodium sulfate in ethanol yields a Y,Y-benzene diamine which in the presence of a reducing agent opens the C=N double bond. In the presence of concentrated acid and heat or in the presence of potassium carbonate and $BrCH_2CO_2$ Ethanol this results in the 2 hydroxyaryl aryl diamine diacetic acid.

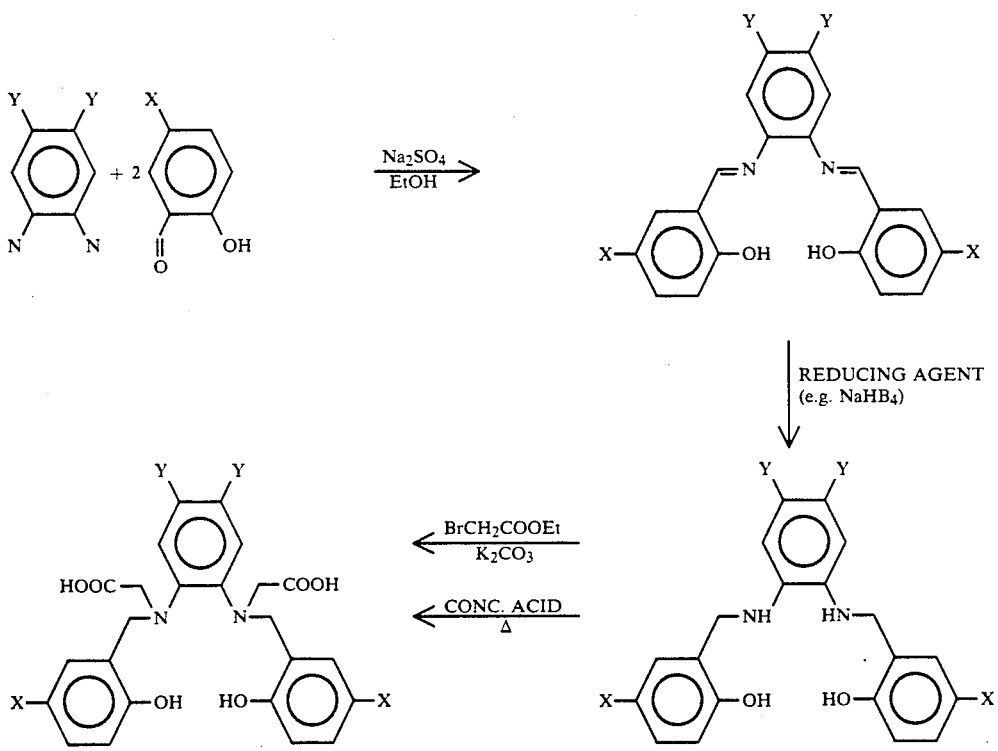

Three-Nitrogen Chelates Having Two Aryl Groups

The formation of chelates having 2 hydroxy aryl groups on a three-nitrogen backbone can proceed along one of the following two pathways, depending upon whether the beginning compound is a diamine or is an amine carboxylate.

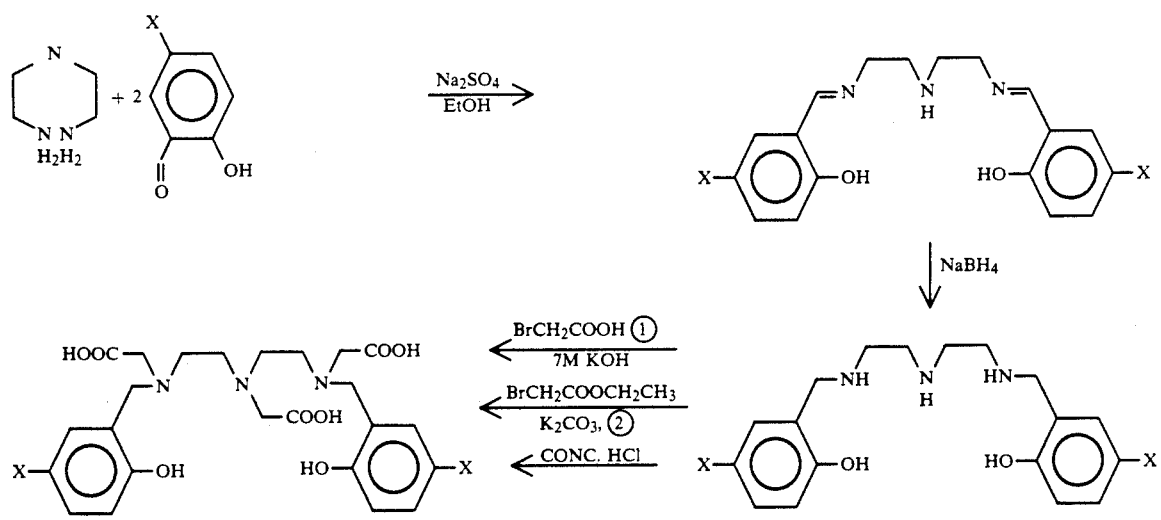

A diamine can be reacted with a benzaldehyde in the presence of sodium sulfate in ethanol to add the 2-hydroxy benzyl groups to the terminal amines of the diamine. The C=N double bond is then reduced and the carboxylate groups added in either of two ways. The reactions are shown above.

Beginning with an amine carboxylate, a methyl group can be added to the carboxylate group by adding the amine carboxylate to methanol under acidic conditions. The terminal hydroxy groups of the amine are tosylated to form DTTMA. Under acidic conditions this then becomes DTTA to which the required aryl groups can be added in either of two ways. The reactions are as follows.

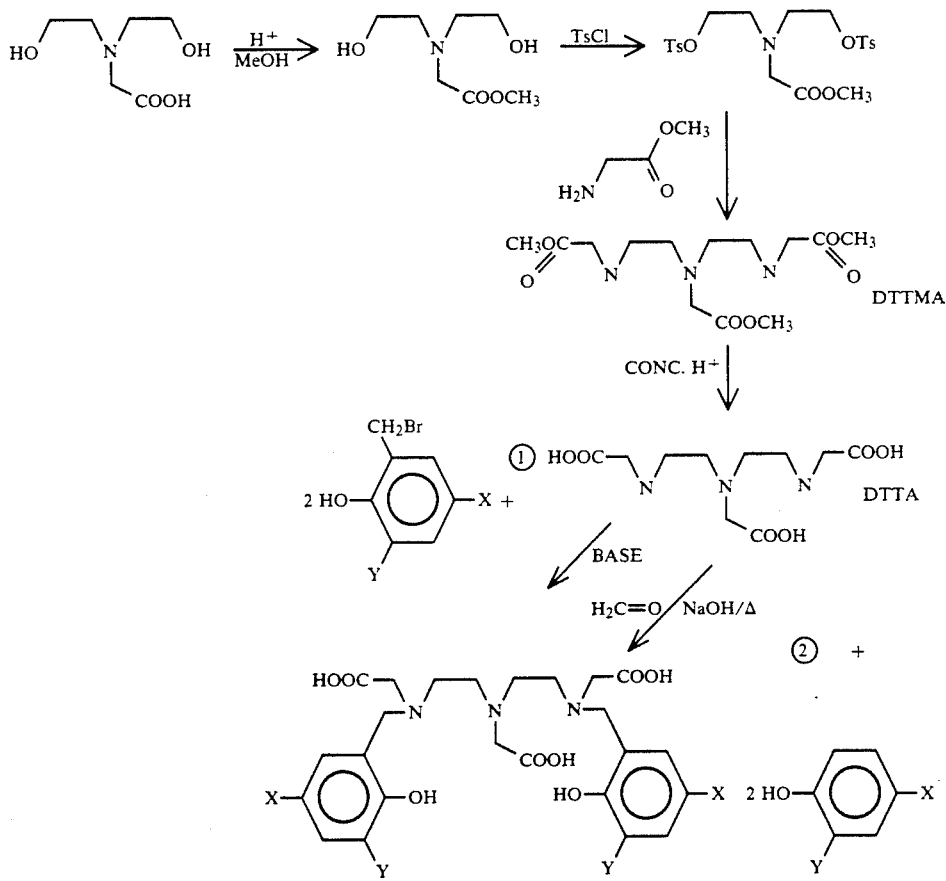

Cyclic Four-Nitrogen Compounds Having One or Two Aryl Rings

Cyclic four-nitrogen chelates having one or two aryl rings are synthesized by reactions proceeding as follows, beginning with methoxyanaline in the presence of ethylene oxide and acetic acid.

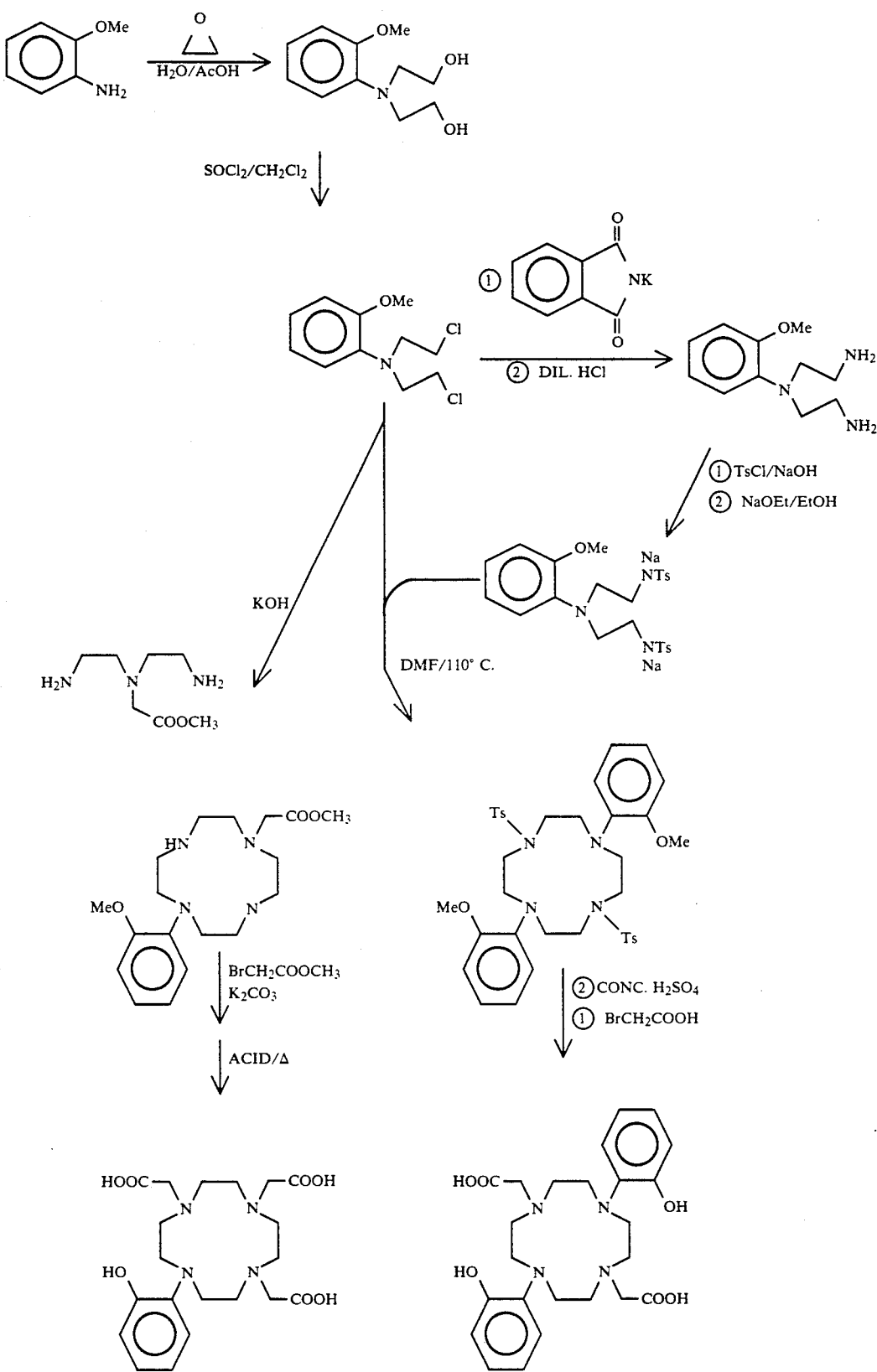
Use
The NMR contrast agents of the invention can be used for enhancing NMR image contrast, by administering the agent to the patient and then carrying out conventional NMR imaging.

A selected contrast agent is administered orally or intravascularly or intraperitoneally in physiological buffer. The agent is selected for high stability, low toxicity, high in vivo relaxivity, and high uptake in the particular target tissue. Dosage depends on the sensitivity of the NMR imaging instrumentation, as well as on the composition of the contrast agent. Preferably, for example, the agent is administered intravenously in a dosage range from about 1-500 μmol/kg.

Following administration of the contrast agent, conventional NMR imaging is carried out. Pulse sequence (inversion recovery, IR; spin echo, SE) and imaging parameter values (echo time, TE; inversion time, TI; repetition time, TR) are selected according to the diagnostic information sought. In general, a $T_1$-weighted image is preferred, and TE preferably is less than 30 milliseconds (or the minimum value) to maximize $T_1$-weighting. Conversely, if a $T_2$-weighted image is desired, then TE should be greater than 30 milliseconds to minimize competing $T_1$ effects. TI and TR will remain approximately the same for both $T_1$- and $T_2$-weighted images; TI and TR are generally on the order of about 200-600 and 100-1000 milliseconds, respectively.

The use of the NMR contrast agents of the invention for image enhancement is illustrated by the following examples, using Fe(BAHBED).

To demonstrate albumin binding and enhancement of relaxivity in vitro, a solution of Fe(BAHBED) was dialyzed at 5° against a 4.5% human serum albumin (HSA) solution (phosphate buffer, pH 7.4). The resulting protein solution contained 0.60 mM-Fe-BAHBED bound and 0.125 mM free, converting to a percentage bound of 82%. In separate experiments the relaxivity of the chelate when bound to HSA was determined at 20 MHz and 37°, using methods generally as described in Lauffer et al., 1988, Nucl. Med. Biol., Vol. 15, pp. 45 ff. The longitudinal relaxivity $R_1$ increased from approx 1 $s^{-1}mM^{-1}$ to 2.7 $s^{-1}mM^{-1}$ upon binding.

To demonstrate image enhancement in NMR imaging in vivo, a 242g fasted male Sprague-Dawley rat was anesthetized with ip pentobarbitol (50 mg/kg) and placed in a head coil of a 0.6 T Technicare MR imaging unit. T1-weighted images (TR 200, TE 22 msec) of the liver were acquired before and after injection of 0.125 mmol/kg Fe(BAHBED). A 40% enhancement of the liver signal intensity was obtained in the first post-injection image at 8 min. A slow decrease in intensity was observed subsequently over the 30 min imaging period. These results are consistent with hepatocelluar uptake and excretion of the chelate as observed previously for EHPG derivatives, Lauffer et al., 1985, J. Comp. Ass. Tomog., Vol. 9, pp. 431 ff. and Lauffer et al., 1987, Magn. Res. Med., Vol. 4, pp. 582 ff.

Other embodiments are within the following claims.

We claim:

1. An NMR contrast composition comprising
a metal ion selected from the group consisting of gadoliumium (III), iron (III), manganese (II), manganese (III), chromium (III), copper (II), dysprosium (III), terbium (III), holmium (III), erbium (III), europium (II), and europiium (III), and
a ligand of the formula:

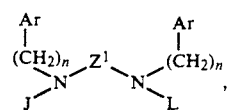

where n is 0 or 1;
each J, L, independently, is

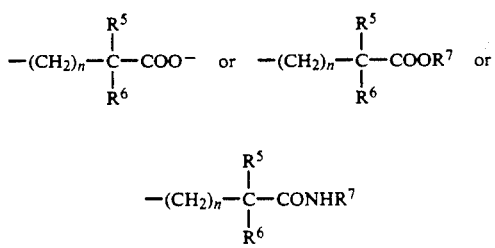

wherein n is 0 or 1;
the aryl groups (Ar) are each one of

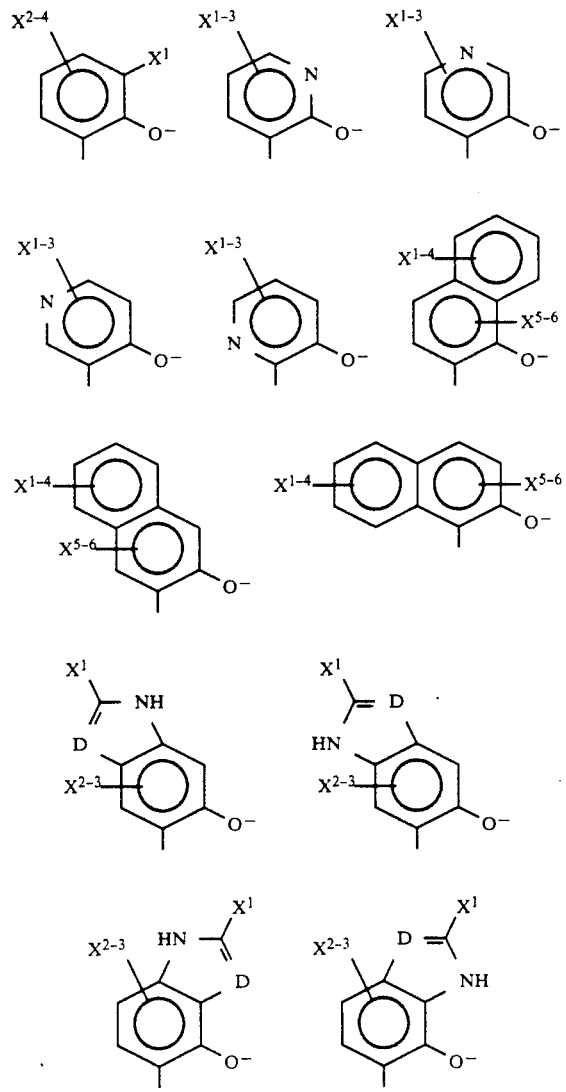

-continued

[Structures: two benzoxazole-type rings with X²⁻³, X¹, H, N, D, O⁻ substituents]

Z¹ is one of

[Structure: R¹\C(R²)−C(R³)/R⁴]

[Structure: benzene ring with X⁷⁻¹⁰]

[Structure: pyridine with X⁷⁻⁹]

[Three pyridine structures with N and X⁷⁻⁹]

[Structures with X⁸⁻⁹, D, X⁷, NH, HN]

[Structures with X⁷, D, NH, HN, X⁸⁻⁹]

[Structures with X⁷, D, NH, HN, X⁸⁻⁹]

[Two naphthalene structures with X⁷⁻¹⁰ and X¹¹⁻¹²]

-continued

[Naphthalene structure with X⁷⁻¹⁰, X¹¹⁻¹²]

[Cyclohexane structure: H₂C−CH₂, H₂C, CH₂, HC−CH]

in which D is one of —CH= or —N=,
each $X^{1-12}$, independently, is one of H, or $C_{1-10}$ alkyl, or $C_{10-15}$ arylalkyl, or halogen, or —(CH$_2$)$_m$COO⁻, or —(CH$_2$)$_m$CONHR$^8$, or —(CH$_2$)$_m$COOR$^8$, or —(CH$_2$)$_m$COH, or —SO$_3$−,
where m is an integer from 0–5,
provided that, where the aryl groups (Ar) have the form

[Structure: benzene with X²⁻⁴, X¹, O⁻]

$X^1$ is one of
—(CH$_2$)$_m$COO⁻, or
—(CH$_2$)$_m$CONHR$^9$, or
—(CH$_2$)$_m$COH, or
—SO$_3$⁻,
and each $X^{2-4}$, independently, is one of
H, or $C_{1-10}$ alkyl, or
$C_{1-10}$ arylalkyl, or halogen;
and each $R^{1-9}$, independently, is one of H, or $C_{1-10}$ alkyl, or $C_{1-15}$ arylalkyl.

2. The composition of claim 1, wherein no more than one of $X^{1-12}$ is a hydrophilic group, said hydrophilic group being ortho to the aryl hydroxy.

3. The composition of claim 2, wherein each of said aryl groups is

[Structure: benzene with X²⁻⁴, X¹, O⁻]

4. The composition of claim 3, wherein n=1 and z is

[Structure: R¹\C(R²)−C(R³)/R⁴]

5. The composition of claim 4, wherein each of $R^{1-4}$ is H, and each of J and L is —CH$_2$—COO⁻.
6. The composition of claim 5, wherein m is 0 of 1.
7. The composition of claim 6, wherein each of $X^{2-4}$ is H or halogen.
8. The composition of claim 7, wherein $X^1$ is COO⁻ or CH$_2$COO⁻, each of $X^2$ and $X^4$ is H, and $X^3$ is halogen.
9. The composition of claim 8, wherein $X^3$ is Br and said metal ion is iron (III).

* * * * *

UNITED STATES PATENT AND TRADEMARK OFFICE
CERTIFICATE OF CORRECTION

PATENT NO. : 5,250,285

DATED : October 5, 1993

INVENTOR(S) : Randall B. Lauffer and Scott K. Larsen

It is certified that error appears in the above-indentified patent and that said Letters Patent is hereby corrected as shown below:

Column 30, claim 1, line 12, replace "$C_{10-15}$" with --$C_{1-15}$--;

Column 30, claim 6, line 60, replace "0 of 1" with --0 or 1--.

Signed and Sealed this

Thirty-first Day of May, 1994

Attest:

BRUCE LEHMAN

Attesting Officer    Commissioner of Patents and Trademarks